(12) United States Patent
Ni et al.

(10) Patent No.: US 10,442,904 B2
(45) Date of Patent: Oct. 15, 2019

(54) METHOD FOR PREPARING CHITOSAN COMPLEX FILM

(71) Applicant: Jiangnan University, Wuxi, Jiangsu (CN)

(72) Inventors: Caihua Ni, Jiangsu (CN); Lei Tao, Jiangsu (CN); Liping Zhang, Jiangsu (CN)

(73) Assignee: JIANGNAN UNIVERSITY, Wuxi, Jiangsu (CN)

( * ) Notice: Subject to any disclaimer, the term of this patent is extended or adjusted under 35 U.S.C. 154(b) by 357 days.

(21) Appl. No.: 15/322,724

(22) PCT Filed: May 27, 2015

(86) PCT No.: PCT/CN2015/079963
§ 371 (c)(1),
(2) Date: Dec. 28, 2016

(87) PCT Pub. No.: WO2016/155107
PCT Pub. Date: Oct. 6, 2016

(65) Prior Publication Data
US 2017/0130016 A1    May 11, 2017

(30) Foreign Application Priority Data

Apr. 3, 2015   (CN) .................. 2015 1 01590710

(51) Int. Cl.
| | |
|---|---|
| *C08J 5/18* | (2006.01) |
| *C08L 5/08* | (2006.01) |
| *A61L 31/04* | (2006.01) |
| *A61L 31/16* | (2006.01) |
| *B29C 39/00* | (2006.01) |
| *B29C 39/14* | (2006.01) |
| *B29C 39/38* | (2006.01) |
| *C08L 31/06* | (2006.01) |
| *C08B 37/08* | (2006.01) |
| *A61K 49/18* | (2006.01) |
| *D01F 9/00* | (2006.01) |
| *B29K 29/00* | (2006.01) |
| *B29L 7/00* | (2006.01) |

(52) U.S. Cl.
CPC .............. *C08J 5/18* (2013.01); *A61L 31/041* (2013.01); *A61L 31/16* (2013.01); *B29C 39/003* (2013.01); *B29C 39/14* (2013.01); *B29C 39/38* (2013.01); *C08L 5/08* (2013.01); *C08L 31/06* (2013.01); *A61K 49/1863* (2013.01); *A61L 2300/232* (2013.01); *A61L 2300/412* (2013.01); *A61L 2300/418* (2013.01); *A61L 2300/424* (2013.01); *A61L 2430/00* (2013.01); *B29K 2005/00* (2013.01); *B29K 2029/04* (2013.01); *B29L 2007/008* (2013.01); *C08B 37/003* (2013.01); *C08J 2305/08* (2013.01); *C08J 2329/04* (2013.01); *D01F 9/00* (2013.01)

(58) Field of Classification Search
CPC ...... C08J 5/18; C08J 2305/08; C08J 2329/04; C08L 31/06; C08L 5/08; B29C 39/003; B29C 39/14; B29C 39/38; A61L 31/041; A61L 31/16; A61L 2430/00; A61L 2300/424; A61L 2300/232; A61L 2300/412; A61L 2300/418; B29L 2007/008; B29K 2005/00; B29K 2029/04; C08B 37/003; A61K 49/1863; D01F 9/00
See application file for complete search history.

(56) References Cited

U.S. PATENT DOCUMENTS

| | | | | |
|---|---|---|---|---|
| 3,962,158 A * | 6/1976 | Mima | .................... | B01D 71/08 524/29 |
| 5,646,206 A * | 7/1997 | Coffin | ........................ | C08J 5/18 524/27 |
| 5,658,592 A * | 8/1997 | Tanihara | ................. | A61L 15/44 424/488 |
| 5,980,883 A * | 11/1999 | Tanihara | ............ | A61K 47/6903 424/78.08 |
| 6,509,039 B1 * | 1/2003 | Nies | ....................... | C08B 37/003 424/422 |
| 7,067,575 B2 * | 6/2006 | Kitamura | ................... | C08J 5/18 524/386 |
| 8,268,914 B2 * | 9/2012 | Verrall | ....................... | C08J 5/18 524/10 |

(Continued)

FOREIGN PATENT DOCUMENTS

| | | |
|---|---|---|
| CN | 101007243 A | 8/2007 |
| CN | 101798393 A | 8/2010 |

(Continued)

*Primary Examiner* — Jeffrey M Wollschlager

(74) *Attorney, Agent, or Firm* — Han IP PLLC; Andy M. Han

(57) ABSTRACT

A method for preparing a chitosan complex film comprises: (1) reacting polyvinyl alcohol-124 with butanedioic anhydride to obtain a modified polyvinyl alcohol; (2) formulating the modified polyvinyl alcohol-124 into a 0.4 wt % aqueous solution, then adding the aqueous solution containing 0.4 wt % of modified polyvinyl alcohol-124 dropwise into an acetic acid solution at a concentration of 0.4 wt % chitosan to obtain a mixed solution; (3) adjusting the pH value of the mixed solution with a 0.01 wt % NaOH solution to pH 5.5, and removing surface bubbles after standing for one hour to obtain a casting solution; (4) pouring the casting solution into a culture dish, placing the culture dish into an oven at 60° C. and drying to a constant weight to obtain the chitosan complex film. The materials used in the method are inexpensive, and the reaction is not complicated, so the cost of the product is not high.

7 Claims, 4 Drawing Sheets

(56) References Cited

U.S. PATENT DOCUMENTS

| | | | | |
|---|---|---|---|---|
| 10,100,215 B2* | 10/2018 | Zischka | ............... | B65D 65/42 |
| 2008/0110370 A1 | 5/2008 | Verrall et al. | | |
| 2008/0146481 A1* | 6/2008 | Brown | ............... | C11D 17/042 |
| | | | | 510/224 |
| 2008/0176985 A1* | 7/2008 | Verrall | ................ | C08J 5/18 |
| | | | | 524/421 |
| 2010/0152430 A1* | 6/2010 | Chen | ................ | C08B 37/003 |
| | | | | 536/20 |
| 2013/0035567 A1* | 2/2013 | Strano | ............... | A61B 5/14532 |
| | | | | 600/316 |
| 2016/0128947 A1* | 5/2016 | McConville | ......... | A61K 31/522 |
| | | | | 424/443 |
| 2016/0235863 A1* | 8/2016 | Gao | ................ | C08B 37/003 |
| 2017/0071873 A1* | 3/2017 | Mousa | ............... | A61K 31/01 |

FOREIGN PATENT DOCUMENTS

| | | |
|---|---|---|
| CN | 102671555 A | 9/2012 |
| EP | 0275100 B1 | 6/1992 |
| WO | WO 2011099460 A1 | 8/2011 |

* cited by examiner

METHOD FOR PREPARING CHITOSAN COMPLEX FILM

CROSS REFERENCE TO RELATED APPLICATIONS

This application is the U.S. national phase application of International application number PCT/CN2015/079963, filed on 27 May 2015, which claims the priority benefit of China Patent Application No. 2015101590710, filed on 3 Apr. 2015. The above-identified applications are hereby incorporated by reference in their entirety.

TECHNICAL FIELD

The present disclosure generally relates to a method of preparing a chitosan complex film and, more particularly, to a low-cost, high quality chitosan complex films casted from a homogeneous mixture of chitosan and polyvinyl alcohol.

BACKGROUND

Development of postoperative tissue adhesions is a common concern and a consequence of a pathophysiological process of healing following a surgery. Postoperative adhesions and scar formations are a major cause of serious complications including peritoneal adhesions, tendon adhesions, soft tissue adhesions after orbital injury and peripheral nerve adhesions, hence hindering a healthy recovery of a human body. Formations of adhesions are remarkable post operations of cardiac surgery, gynecological surgery and orthopedic surgery. Common methods of preventing adhesion formations are medical treatments to inhibit fibroblastic proliferations, biological therapies, better surgical techniques, and barriers placed in between tissues.

The chitosan (CS) is a natural alkaline polysaccharide and is produced by deacetylation of chitin. Chitosan has found many biomedical uses with distinct benefits of being biocompatible, biodegradable, antibacterial and hemostatic, as well as capability of boosting tissue regeneration and strong cellular adherence. Considerable amounts of studies of chitosan in recent years have shown characteristics of chitosan in preventing postoperative adhesions and reducing fibroblastic growth on damaged tissues either in a form of film or gel.

Complex polyelectrolyte films have emerged as important components of new membrane materials with wide applications such as in phase separation, nanofiltration, fruit preservation, and biomedicine. However, pure chitosan films formed as a type of polyelectrolytes are subject to poor mechanical toughness, fast dissolution and quick degradation while embedded in body fluids. As such, applications of pure chitosan films are restricted to a certain aspect.

The present disclosure describes a method of preparing chitosan complex films to improve properties of chitosan complex films in mechanical toughness and extending the time chitosan complex films take to degrade. Polyvinyl alcohol (PVA) has good biocompatibility, being water soluble, and is a commonly used biomedical material as a protective coating on wounds and an embolization agent in drug delivery. In addition, PVA has good film-forming ability and is compatible with CS, especially having superior mechanical properties as the most remarkable benefits. There are two common methods of preparing complex films of PVA and chitosan, physical blending and chemical cross-linking. A homogeneous solution results after physical blending of PVA and chitosan due to formations of hydrogen bonds between the two polymeric molecules of PVA and chitosan. Chitosan complex films formed from the blended homogeneous solution are easy to swell and prone to fast dissolution in body fluids, resulting in rapid loss of films and less resistive barriers for anti-adhesion purposes. Chitosan complex films prepared by the chemical crosslinking method may have superior performance in applications as medical materials, but often contain harmful chemicals to human as most of the crosslinking agents such as glutaraldehyde are toxic.

SUMMARY

It is the goal of the present disclosure to provide a method for preparing chitosan complex films, which remedies the deficiencies and properties of pure chitosan films and improvises the chitosan complex films for anti-adhesion medical uses.

The technical description of the present disclosure is provided below:

A method of preparing a chitosan complex film, the method includes the steps of:

(1) Obtaining modified polyvinyl alcohol-124 (PVA-124) by reacting PVA-124 with butanedioic anhydride;

(2) Formulating an aqueous solution containing 0.4 wt % of modified PVA-124, then adding the modified PVA-124 solution dropwise into an acetic solution containing 0.4 wt % of chitosan to obtain a mixed solution;

(3) Adjusting the pH value of the mixed solution to pH 5.5 with a 0.01 wt % NaOH solution, obtaining a casting solution by removing surface bubbles of the mixed solution after one hour standing of the mixed solution; and (4) Pouring the casting solution into a culture dish, placing the culture dish into an oven at 60° C. and drying the culture dish with the casting solution until no change in weight to obtain a chitosan complex film.

At step (1) in obtaining of the modified PVA-124 may further include: Formulate a solution with 20 wt % of PVA-124 dissolved in a dimethylsulfoxide solvent and another solution with 20 wt % of butanedioic anhydride dissolved in a dimethylsulfoxide solvent respectively. Mix the 20 wt % PVA-124 solution with the 20 wt % butanedioic anhydride solution according ratios of the OH mole number of butanedioic anhydride to that of PVA-124. Five different ratios of the OH mole number of butanedioic anhydride to the OH mole number of PVA-124 (1:10, 1.25:10, 1.6:10, 2.0:10, and 2.5:10) are formulated for the PVA-124 and butanedioic anhydride mixtures. Mixing of the 20 wt % PVA-124 solution with the 20 wt % butanedioic anhydride solution is conducted at 75° C. and stirred at 800 rounds/min for 5 hours by titrating the butanedioic anhydride solution into the PVA-124 solution. Cool the mixtures to room temperature, slowly adding small volumes of the mixtures into an ethanol solution containing 5~10 wt % of NaOH to form precipitates of modified PVA-124. Rinse the precipitates of modified PVA-124 repeatedly and dry the precipitates at 60° C. in vacuum until no change in weight of the precipitates. Five different precipitates of modified PVA-124 named SP1, SP2, SP3, SP4, and SP5 are obtained from five mixtures containing different OH mole number ratios between butanedioic anhydride and PVA-124 as described above.

The step (2) further includes the following details. Formulate aqueous solutions containing 0.4 wt % of SP1, SP2, SP3, SP4, or SP5 respectively and add each aqueous solution dropwise into an equal-mass acetic solution containing 0.4 wt % of chitosan to obtain five corresponding mixtures with chitosan.

At step (2) in the formulating of aqueous solutions containing 0.4 wt % of SP1, SP2, SP3, SP4, or SP5 respectively and in obtaining corresponding mixtures with acetic solutions containing 0.4 wt % of chitosan may include: Dissolve SP1, SP2, SP3, SP4, or SP5 into deionized water to formulate aqueous solutions containing 0.4 wt % of SP1, SP2, SP3, SP4, or SP5 respectively. Formulate the acetic solution by dissolving 0.4 wt % of chitosan in 1 wt % acetic acid. Filter the acetic solution containing 0.4 wt % of chitosan with a syringe-like filter having a 0.45 μm diameter to remove the fractional amounts of insoluble impurities. Add small volumes (dropwise) of the aqueous solutions containing SP1, SP2, SP3, SP4, or SP5 into the acetic solution containing 0.4 wt % of chitosan respectively and stir at 1000 rounds/minute to form a homogeneous mixture.

At step 3, the pH value of the homogeneous mixture of chitosan and modified PVA-124 (SP1, SP2, SP3, SP4, and SP5) is adjusted to pH 5.5 by a 0.01 wt % NaOH solution. The surface bubbles of the pH 5.5 mixture are removed after standing for an hour to obtain a casting solution.

The present disclosure provides a method of preparing a chitosan complex film with the following merits:

(1) The carboxyl radicals of PVA are modified due to reactions with butanedioic anhydride. The modified PVA product and chitosan molecules form stronger ionic bonds in addition to hydrogen bonds, improving the stability and mechanical properties of chitosan complex films while embedded in the body fluids. As such, the chitosan complex films are suitable for anti-adhesion medical use.

(2) Pure chitosan films are prone to quick degradation and subject to film loss from wounds, lessening the effectiveness of anti-adhesion. Chitosan complex films formed with modified PVA-124 are resistive to degradation and a more effective barrier in anti-adhesion applications.

(3) PVA-124 and chitosan materials selected in the present disclosure have been shown good biocompatibilities. The present disclosure uses modified PVA-124 and chitosan to form complex films. The modified PVA-124 is obtained by a reaction between PVA-124 and small molecules of butanedioic anhydride. The residual, unreacted small molecules of butanedioic anhydride after the reaction are removed and the reaction product is also nontoxic and biocompatible, suitable to be implanted in a human body as far as the safety is concerned.

(4) The materials or chemicals needed in the present disclosure to form chitosan complex films are low cost and the reactions are not complicated. Such films are affordable and likely accepted by most patients.

BRIEF DESCRIPTION OF THE DRAWINGS

To more clearly illustrate the embodiments of the present disclosure, the drawings which are required to be used in the description of the embodiments will be briefly described below. It will be apparent that the drawings described below are only some, not all, of embodiments of the present disclosure. One of ordinary skill in the art may derive other drawings without inventive workability according to the drawings described below.

Non-limiting and non-exhaustive embodiments of the present disclosure are described with reference to the following figures, wherein like reference numerals refer to like parts throughout the various figures unless otherwise specified.

DETAILED DESCRIPTION OF THE PREFERRED EMBODIMENTS

Figure 1:
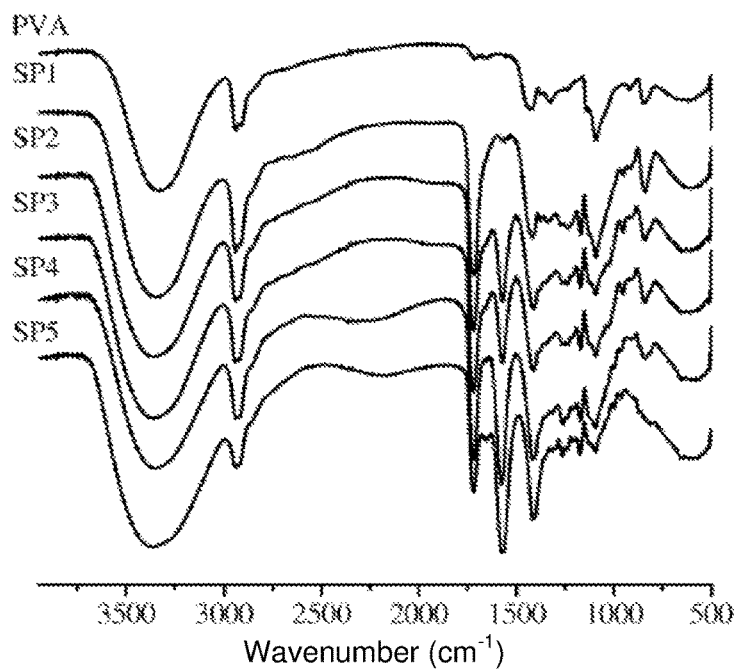
FIG. 1 is a collection of infrared spectra of PVA before and after modification prepared according to the method of the present disclosure.

In accordance with the present disclosure, the method of preparing a chitosan complex film includes steps of:

(1) Obtaining modified PVA-124 by reacting PVA-124 with butanedioic anhydride;

(2) Formulating an aqueous solution containing 0.4 wt % of modified PVA-124, then adding the modified PVA-124 solution dropwise into an acetic solution containing 0.4 wt % of chitosan to obtain a mixed solution;

(3) Adjusting the pH value of the mixed solution to pH 5.5 with a 0.01 wt % NaOH solution, obtaining a casting solution by removing surface bubbles of the mixed solution after one hour standing of the mixed solution; and (4) Pouring the casting solution into a culture dish, placing the culture dish into an oven at 60° C. and drying the culture dish with the casting solution until no change in weight to obtain a chitosan complex film.

Detail descriptions of the present disclosure described above are followed to further illustrate the characteristics and excellency of the method provided by the present disclosure.

A method of preparing a chitosan complex film, including:

Step (1): Obtaining modified PVA-124 by reacting PVA-124 with butanedioic anhydride;

In one embodiment, step (1) performs the following: Formulate a solution containing 20 wt % of PVA-124 dissolved in a dimethylsulfoxide solvent and another solution containing 20 wt % of butanedioic anhydride dissolved in a dimethylsulfoxide solvent respectively. Mix the 20 wt %

PVA-124 solution with the 20 wt % butanedioic anhydride solution according ratios of the OH mole number of butanedioic anhydride to that of PVA-124. Five different ratios of the OH mole number of butanedioic anhydride to the OH mole number of PVA-124 (1:10, 1.25:10, 1.6:10, 2.0:10, and 2.5:10) are formulated for the PVA-124 and butanedioic anhydride mixtures. Mixing of the 20 wt % PVA-124 solution with the 20 wt % butanedioic anhydride solution is conducted at 75° C. and stirred at 800 rounds/min for 5 hours by titrating the butanedioic anhydride solution into the PVA-124 solution. Cool the mixtures to room temperature, slowly adding small volumes of the mixtures into an ethanol solution containing 5~10 wt % of NaOH to form precipitates of modified PVA-124. Rinse the precipitates of modified PVA-124 repeatedly and dry the precipitates at 50° C. in a vacuum until no change in weight of the precipitates. Five different precipitates of modified PVA-124 named SP1, SP2, SP3, SP4, and SP5 are obtained from five mixtures containing different OH mole number ratios between butanedioic anhydride and PVA-124 as described above.

Step (2): Formulating an aqueous solution containing 0.4 wt % of modified PVA-124, then adding the modified PVA-124 solution dropwise into an acetic solution containing 0.4 wt % of chitosan to obtain a mixed solution;

In one embodiment, step (2) performs the following: Dissolve SP1, SP2, SP3, SP4, or SP5 into deionized water to formulate aqueous solutions containing 0.4 wt % of SP1, SP2, SP3, SP4, or SP5 respectively. Formulate the acetic solution by dissolving 0.4 wt % of chitosan in 1 wt % acetic acid. Filter the acetic solution containing 0.4 wt % of chitosan with a syringe-like filter having a 0.45 μm diameter to remove the fractional amounts of insoluble impurities. Add small volumes (dropwise) of the aqueous solutions containing SP1, SP2, SP3, SP4, or SP5 into the acetic solution containing 0.4 wt % of chitosan respectively and stir at 1000 rounds/minute to form a homogeneous mixture.

Step (3): Adjusting the pH value of the mixed solution to pH 5.5 with a 0.01 wt % NaOH solution, obtaining a casting solution by removing surface bubbles of the mixed solution after one hour standing of the mixed solution; and Step (4): Pouring the casting solution into a culture dish, placing the culture dish into an oven at 60° C. and drying the culture dish with the casting solution until no change in weight to obtain a chitosan complex film.

Embodiments in accordance with the present disclosure and figures are described below to further illustrate the characteristics and excellency of the method provided by the present disclosure. Embodiments and figures are for illustrative purposes only and without limitations, as claims include variations of embodiments and figures known to one of ordinary skill of at.

Firstly, references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Secondly, the present disclosure uses structural schematic diagrams or the like to describe details. While the embodiments of the present disclosure have been described in detail, the illustrations are not drawn proportionally in scale for the convenience of explanation, and are merely illustrative and should not be construed as limiting the scope of the present disclosure. The three-dimensional space shall include length, width and depth.

In addition, the acronyms or abbreviations used in the present disclosure are known to one of ordinary skill of art in the same technical field. Some of the representative acronyms are: PVA: polyvinyl alcohol; CS: chitosan.

Embodiment 1

Synthesis of Modified PVA-124

Formulate a solution containing 20 wt % of PVA-124 dissolved in a dimethylsulfoxide solvent and another solution containing 25 wt % of butanedioic anhydride dissolved in a dimethylsulfoxide solvent respectively. Mix the 20 wt % PVA-124 solution with the 20 wt % butanedioic anhydride solution according to ratios of the OH mole number of butanedioic anhydride to that of PVA-124. Five different ratios of the OH mole number of butanedioic anhydride to the OH mole number of PVA-124 (1:10, 1.25:10, 1.6:10, 2.0:10, and 2.5:10) are formulated for the PVA-124 and butanedioic anhydride mixtures. Mixing of the 20 wt % PVA-124 solution with the 20 wt % butanedioic anhydride solution is conducted at 75° C. and stirred at 800 rounds/min for 5 hours by titrating the butanedioic anhydride solution into the PVA-124 solution. Cool the mixtures to room temperature, slowly adding small volumes of the mixtures into an ethanol solution containing 5~10 wt % of NaOH to form precipitates of modified PVA-124. Rinse the precipitates of modified PVA-124 repeatedly and dry the precipitates at 50° C. in a vacuum until no change in weight of the precipitates. Five different precipitates of modified PVA-124 named SP1, SP2, SP3, SP4, and SP5 are obtained from five mixtures containing different OH mole number ratios between butanedioic anhydride and PVA-124 as described above.

TABLE 1

Synthesis of modified PVA-124 and analytical results

| Sample | butanedioic anhydride:PVA-124-OH mole ratio | Conversion of OH to COOH (%) of the precipitates |
|---|---|---|
| SP1 | 1.00:1.0 | 8 |
| SP2 | 1.25:1.0 | 11 |
| SP3 | 1.60:1.0 | 15 |
| SP4 | 2.00:1.0 | 19 |
| SP5 | 2.50:1.0 | 24 |

Embodiment 2

Infrared Spectrum Analysis of Modified PVA-124

The modified PVA-124 of Table 1 are characterized by Fourier Transform Infrared Spectroscopy (FTIR) to measure its infrared absorption spectrum in the wavenumber range between 4000~500 cm$^{-1}$, with a resolution of 4 cm$^{-1}$. FIG. 1 shows FTIR absorption spectra of PVA and modified PVA-124 of SP1, SP2, SP, SP4, and SP5. As depicted in FIG. 1, the absorption peaks of —OH bonds in modified PVA-124 appear around 3200~3600 cm$^{-1}$ wavenumber whereas the absorption peaks at 2930 cm$^{-1}$ are associated with anti-symmetrical stretching vibrations of —CH$_2$ bonds and the absorption peaks at 1450 cm$^{-1}$ are associated with the symmetric twisting vibrations of —CH$_2$ bonds. After PVA-124 is modified by a reaction with butanedioic anhydride, absorption peaks of symmetrical stretching vibrations of C=O bonds appear at the vicinity of 1750 cm$^{-1}$ and the characteristic absorption peaks of carboxylate appear at 1580 cm$^{-1}$ and 1408 cm$^{-1}$. Such characteristic absorption peaks of carboxylate are attributed to the successful modification of PVA-124. In addition, the progressive wider, stronger, and shifting wavelength toward higher wavenumbers of —OH absorption peaks are correlated to the amounts of butanedioic anhydride reacted with PVA-124. Such changes of absorption peaks of —OH bonds indicate that the extent of carboxylation increases with the amount of butanedioic anhydride.

Embodiment 3

Nuclear Magnetic Resonance (1H-NMR) Analysis of Modified PVA-124

Figure 2:
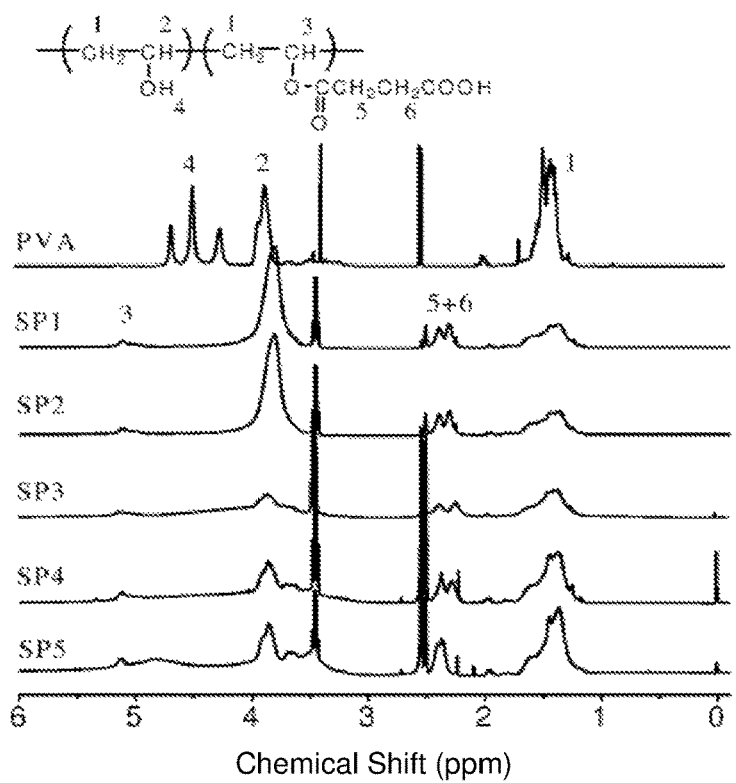
FIG. 2 is a nuclear magnetic resonance spectra of PVA before and after modification prepared according to the method of the present disclosure.

Referring to FIG. 2, an 1H-NMR analysis of modified PVA-124 is conducted on sample solutions containing 10 mg/ml of modified PVA-124 dissolved in deuterated dimethyl sulfoxide (DMSO) with tetramethylsilane (TMS) as an internal standard. The 1H-NMR resonance spectra of PVA and modified PVA-124 of SP1, SP2, SP3, SP4, and SP5 used in preparing a chitosan complex film is shown in FIG. 2, in which the DMSO peak at $\delta 2.50$, the water peak at $\delta 3.50$, and the TMS peak at $\delta 0$ are observed. The various proton peaks of PVA-124 in FIG. 2 are $CH_2$ at $\delta 1.10 \sim \delta 1.70$, CH at $\delta 3.70 \sim \delta 3.97$, and OH at $\delta 4.15 \sim \delta 4.70$ respectively. After PVA-124 is modified by a reaction with butanedioic anhydride, the proton peaks of CH appear around $\delta 4.8 \sim \delta 5.20$ and a formation of multiple peaks around $\sim 2.24 \sim \delta 2.49$ is due to overlaps of proton peaks of $CH_2$ in butanedioic anhydride and $CH_2$ in modified PVA-124. The presence of these peaks is reasonably explained by a successful reaction of modifying PVA-124 with butanedioic anhydride.

Embodiment 4

Thermogravimetric Analysis of Modified PVA-124

Figure 3:
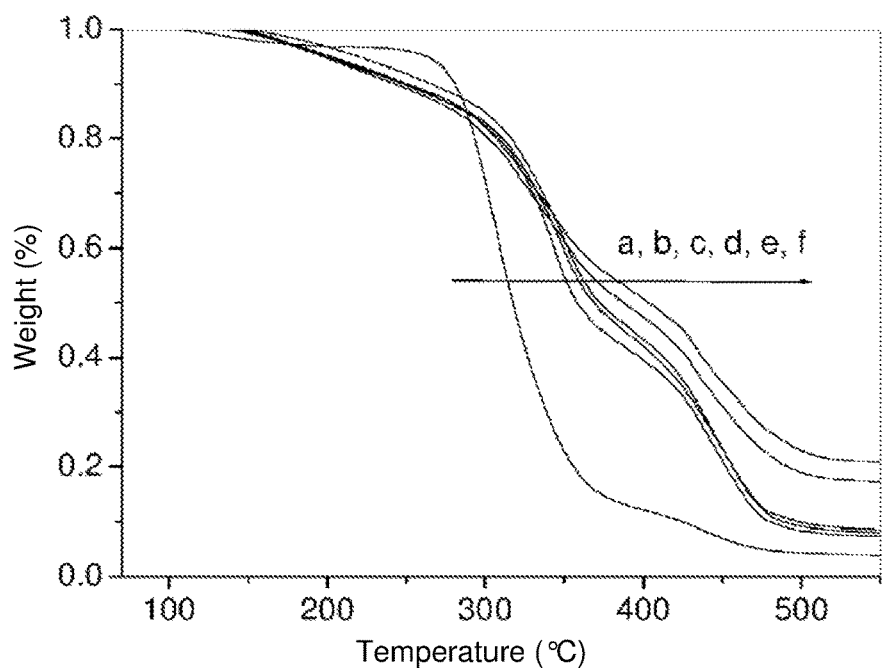
FIG. 3 is a collection of thermogravimetric traces of PVA before and after modification prepared according to the method of the present disclosure; a is PVA, b is SP1, c is SP2, d is SP3, e is SP4, f is SP5.

FIG. 3 shows thermogravimetric curves of PVA before and after modification used in preparing a chitosan complex film. Referring to FIG. 3, the thermogravimetric curves a, b, c, d, e, f are from PVA and modified PVA-124 of SP1, SP2, SP3, SP4, and SP5 respectively. The mass loss of PVA may be divided into three stages. The first stage is the thermal decomposition of the main branch of PVA, occurring around 250~400° C. The second stage is the continuing thermal decomposition of remaining terminal alkyne from the decomposed main branch into carbon and hydrocarbons, occurring around 400° C. Comparing with modified PVA-124, the temperatures at which the thermal decomposition of the main branches of modified PVA-124 are lower and the residual masses in the second stage are larger. The succinate radicals in modified PVA-124 increase as the extent of carboxylation grows, as a result of which, more butanedioic acid and water are produced, promoting the replacement of —OH with unstable —$OH^{2+}$ on the main branches of modified PVA-124 and accelerating the thermal decomposition of the main branches.

Embodiment 5

A Method of Preparing a Chitosan Complex Film

Dissolve 2 grams of chitosan (CS, 96.4% degree of deacetylation) in 498 ml, 1.0 wt % acetic aqueous solution homogeneously. Filter the solution with a syringe-like filter having a 0.45 μm to remove fractional insoluble impurities. Dissolve SP1 of modified PVA-124 in deionized water to formulate a 500 ml aqueous solution containing 0.4 wt % of SP1. Add small volumes (dropwise, titrating) of 50 grams, 0.4 wt % SP1 aqueous solution into 50 grams, 0.4 wt % chitosan acetic solution and stir the titrated solutions to obtain a homogeneous mixture. Adjust the pH value of the homogeneous mixture of SP1 and chitosan with a solution containing 0.01 wt % NaOH to pH 5.5, remove surface bubbles of the homogeneous mixture after standing for 5 hours to obtain a casting solution. Pour the casting solution into a 12 cm×12 cm culture dish, incubate the culture dish at 60° C. until no change in weight to obtain a complex film of chitosan (CS/SP1).

Replace SP1 with SP2, SP3, SP4, and SP5 respectively and four other chitosan complex films named CS/SP2, CS/SP3, CS/SP4, and CS/SP5 are prepared from performing the same steps described above.

Embodiment 6

Mechanical Properties of Chitosan Complex Films

Two test specimen of chitosan complex films are prepared according to GBT 1040.3-2006 standards. Mechanical properties are measured by tensile test machine on test specimen at 25° C. and RH (a relative humidity) 50% with an elongation rate 5 mm/min.

TABLE 2

Mechanical Properties of Chitosan complex film

| | Dry film | | Wet film | |
|---|---|---|---|---|
| Specimen | Tensile Strength (MPa) | Elongation at break (%) | Tensile Strength (MPa) | Elongation at break (%) |
| CS/SP1 | 35.42 | 13.07 | 3.56 | 17.43 |
| CS/SP2 | 38.64 | 12.59 | 4.08 | 19.37 |
| CS/SP3 | 40.76 | 11.42 | 4.97 | 20.06 |
| CS/SP4 | 44.36 | 11.39 | 5.52 | 21.71 |
| CS/SP5 | 47.42 | 10.64 | 6.07 | 24.15 |

Embodiment 7

Infrared Spectrum of a Chitosan Complex Film

Figure 4:
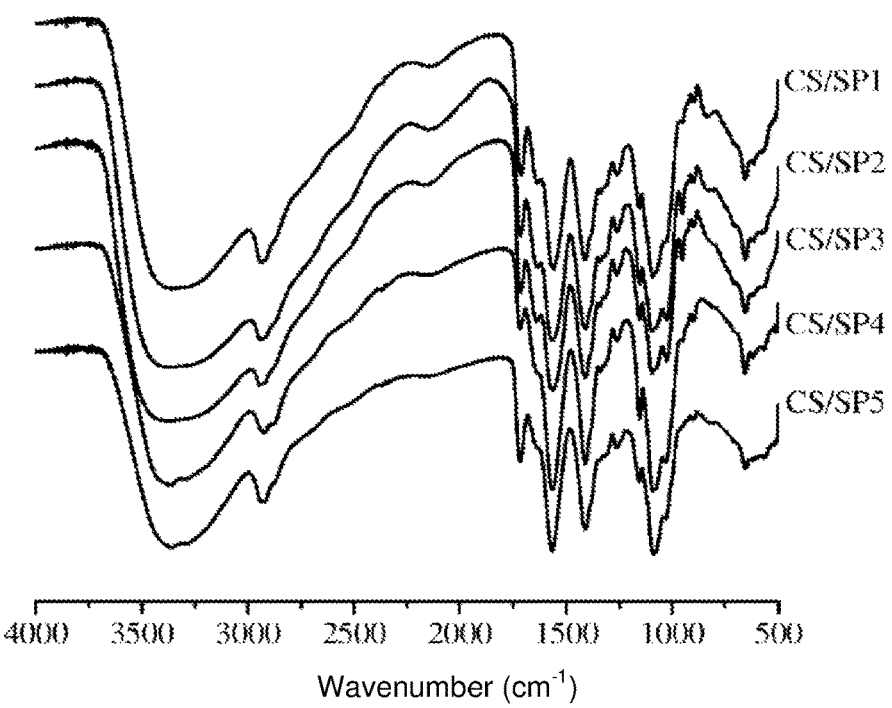
FIG. 4 is a collection of infrared spectra of chitosan complex films prepared by mixing 0.4 wt % of chitosan acetic solutions with equal-mass aqueous solutions containing 0.4 wt % of different modified PVA-124 according to the method of the present disclosure.

Characterize five chitosan complex films of CS/SP1, CS/SP2, CS/SP3, CS/SP4 and CS/SP5 obtained from the embodiment 5 above with Fourier Transform Infrared Spectroscopy (FTIR) within a range of 4000~500 $cm^{-1}$, with a resolution of 4 $cm^{-1}$. FIG. 4 shows FTIR infrared spectra of chitosan complex films obtained by mixing an equal mass of a 0.4 wt % modified PVA-124 solution and an acetic solution containing 0.4 wt % of chitosan. After formation of chitosan complex films, the characteristic peaks of O—H, N—H in CS molecules and C=O of amide radicals, as well as C—O in SP (SP1, SP2, SP3, SP4, or SP5) molecules are shifted, which is associated with the formation of hydrogen bonds between CS and SP molecules. Furthermore, the twisting vibrational peak of N—H in CS is shifted towards higher wavenumbers and overlaps with the peak of C=O in carboxylate, which may be explained by the transformation of —$NH_2$ into —$NH^{3+}$. Thus, it is possible that the ionic bonds are formed between CS and modified PVA-124.

Embodiment 8

Thermogravimetric Analysis of Chitosan Complex Films

Figure 5:
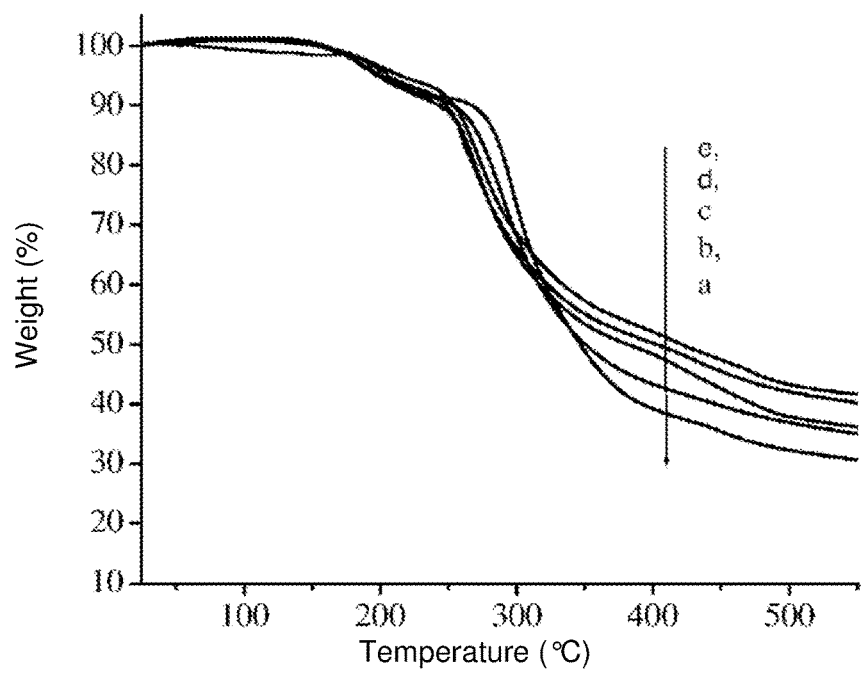
FIG. 5 is a collection of thermogravimetric traces of chitosan complex films prepared according to the method of the present disclosure, a is CS/SP1, b is CS/SP2, c is CS/SP3, d is CS/SP4, e is CS/SP5.

FIG. 5 shows thermogravimetric curves of chitosan complex films.

Referring to FIG. 5, thermogravimetric curves of CS mixed with SP1, SP3, and SP5 respectively according to a 1:0.3 mass ratio are measured. Two stages of thermal decomposition may be observed from FIG. 5, with the thermal decomposition caused by the dehydration of ions in polyelectrolytes occurring around 100~195° C. The second stage is the thermal decomposition of the main branch. The temperature dependences of thermal decomposition of chitosan complex films are different than those of pure chitosan films, which may be attributed to more uniform structures of the chitosan complex films. It can be observed in FIG. 5 that the temperature at which the rate of thermal decomposition reaches maximum decreases from 260° C. to 236° C. and the remaining mass increases from 30.67% to 41.65% at 550° C.

as the extent of carboxylation grows. The rates of thermal decomposition of chitosan complex films are varying less with respect to the temperature due to more stable structures.

Embodiment 9

Contact Angle Measurement of Chitosan Complex Films

Figure 6:
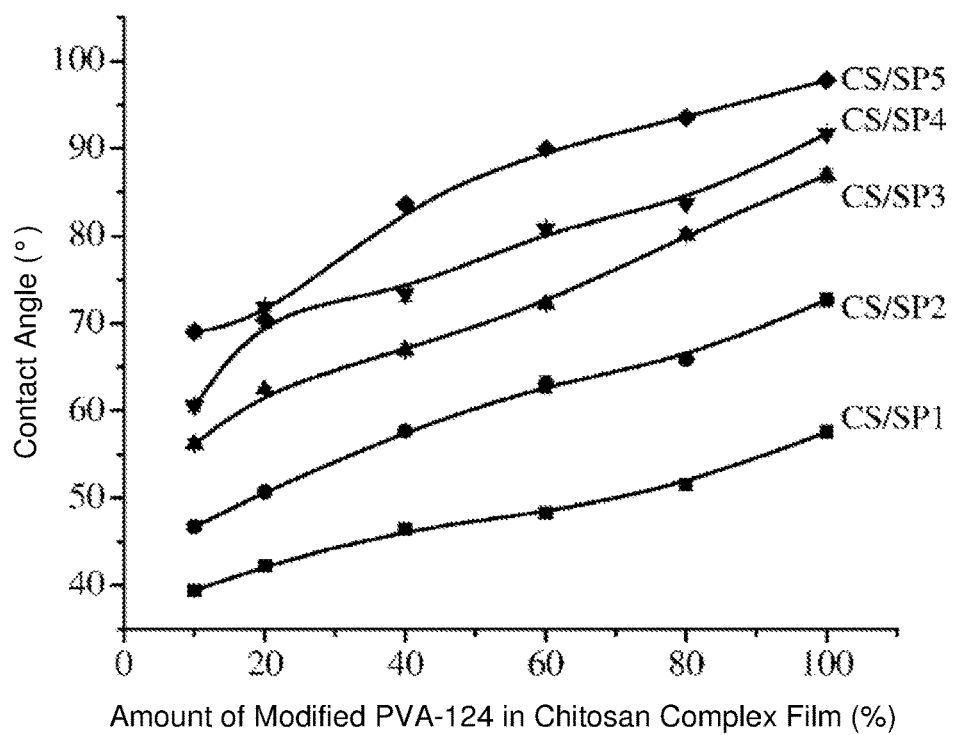
FIG. 6 is a collection of contact angle measurements of chitosan complex films prepared according to the method of the present disclosure.

FIG. 6 shows contact angle measurements of chitosan complex films. Referring to FIG. 6, the contact angle increases with the amount of modified PVA-124 in a chitosan complex film. Such change is related to an increase of polyelectrolyte compounds and a decrease of hydrophilic radicals of $—NH^{3+}$, $—COO—$, and $—OH$. Thus, the hydrophilicity or hydrophobicity of chitosan complex films may be controlled by changing the mass ratio between chitosan and modified PVA-124 to design different chitosan complex films with various contact angles for different biological needs.

Embodiment 10

Equilibrium Swelling Ratio of Chitosan Complex Films in Saline

A square 3 cm×3 cm chitosan complex film is immersed in a 0.9 wt % NaCl solution at a 37° C. constant temperature and agitating bath. The weight of the chitosan complex film is measured after immersed for 6 hours in the NaCl bath and dried by the absorption of filter papers. The square film may reach a state of swelling equilibrium such that its weight no longer changes. The equilibrium swelling ratio $S_o$ of the square film is measured 3 times independently after 6 hours of immersion and the equilibrium swelling ratio may be calculated by the formula:

$$S_0 = \frac{m_b - m_0}{m_0} \times 100\%$$

$m_0$ and $m_b$ are the mass (g) of the complex film before and after swelling respectively.

Figure 7:
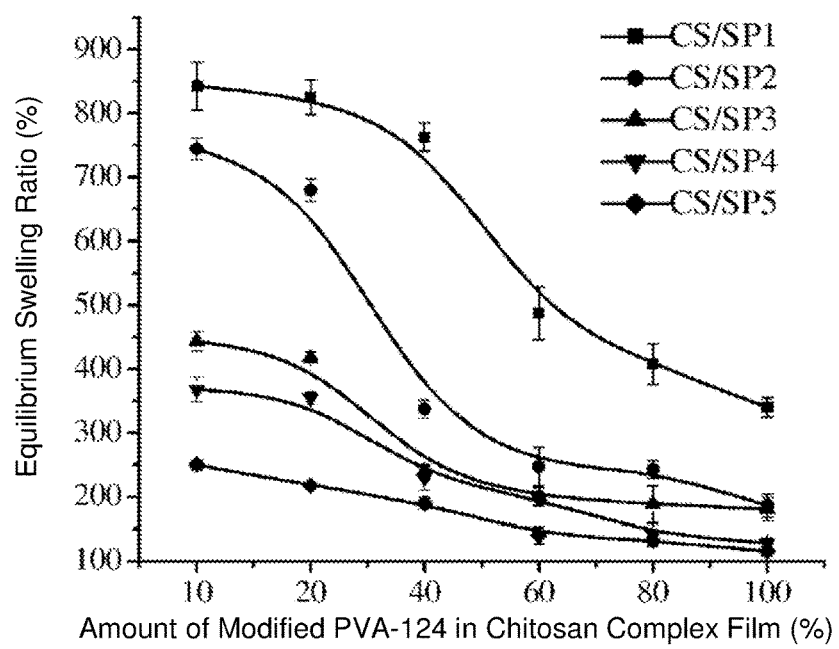
FIG. 7 is a collection of equilibrium swelling ratios in saline of chitosan complex films prepared according to the method of the present disclosure.

FIG. 7 shows equilibrium swelling ratios of chitosan complex films immersed in saline. Referring to FIG. 7, the equilibrium swelling ratio is larger with less amount of modified PVA-124 in the chitosan complex film. This is attributed to repulsions between chitosan molecules carrying a high number of positive charged $—NH^{3+}$, as such, the chitosan film is more stretchable and has a larger equilibrium swelling ratio. The equilibrium swelling ratio deceases with the amount of SP (SP1, SP2, SP3, SP4, or SP5) in the chitosan complex film, which may be due to the increase of electrolyte compounds and the decrease of hydrophilic radicals, $—NH^{3+}$ and $—COO—$, causing a reduction of water absorbability. The decrease of water absorbability of chitosan complex films having a fixed ratio of chitosan (CS) to modified PVA-124 can also be observed as the extent of carboxylation of modified PVA-124 increases. A larger amount of electrolyte compounds is formed when the modified PVA-124 has a higher extent of carboxylation, causing a reduction of equilibrium swelling ratio.

Embodiment 11

In Vitro Cytotoxicity of Chitosan Complex Films

Studies of in vitro cytotoxicity in the presence of chitosan films are performed using the MTT [3-(4,5-dimethylthiazol-2-yl)-2,5-diphenyltetrazolium bromide] assay. Place 2.4× $10^4$ 3T3 cells in growth period into each of 96 wells of a culture vessel. Incubate the 3T3 cells in the culture vessel with a RPMI-1640 culture medium (RPMI-1640 complete culture medium) containing 10% fetal bovine serum at 37° C. and 5% $CO_2$ in an incubator. Remove the culture medium after incubating for 24 hours. After treated with high temperature and sterilization, the chitosan complex films of 6 $cm^2$ of membranes (CS/SP1 and CS/SP5) are placed in saline at 37° C. and the solutions are extracted after 6, 12, 24, and 48 hours. The extractants are diluted with RPMI-1640 culture medium to a concentration of 0.1 µL/µL (1 to 10 ratio) to serve as test samples. Each well in the culture vessel is fed with 100 µL RPMI-1640 complete culture medium, RPMI-1640 culture medium containing 0.64% phenol, and the diluted extractants in sequence to serve as control samples in the negative group, control samples in the positive group and test samples in the test group respectively. Every group consists of 6 wells and all wells are incubated at 37° C. and 5% $CO_2$ for 48 hours. 20 µL MTT is added in each well for another 4 hours of incubation. After crystalline precipitates are dissolved, the absorbance at 570 nm are measured using enzyme-linked immunosorbent assay (ELISA) and cell viabilities of test samples are calculated.

Figure 8:
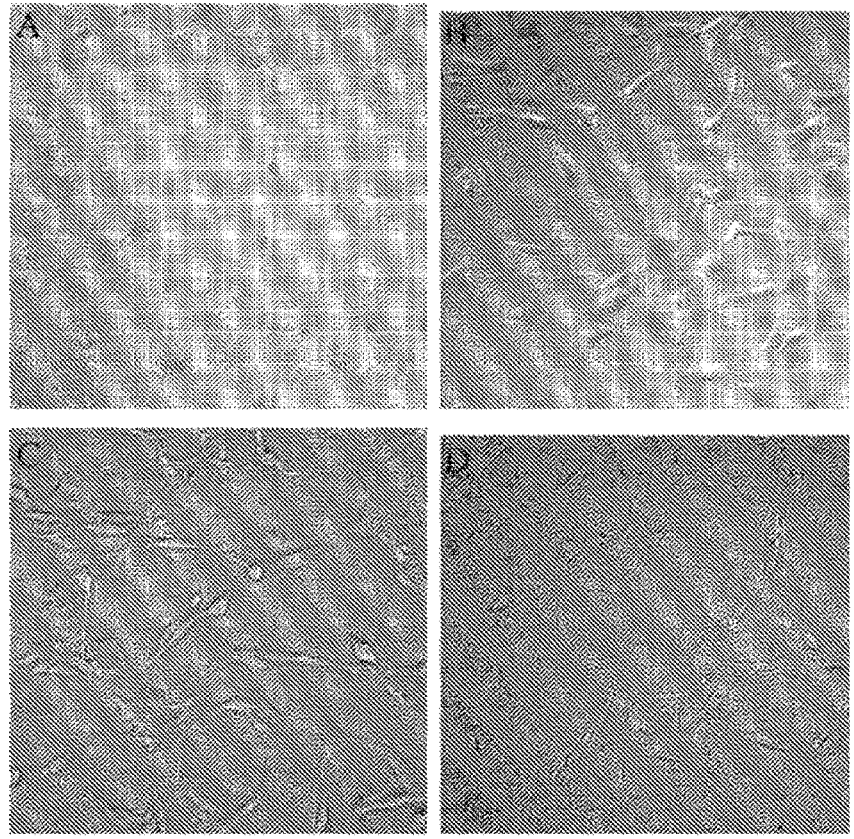
FIG. 8 shows micrographs of 3T3 cells after in vitro cytotoxicity assay using chitosan complex films prepared according to the method of the present disclosure. A is a control sample of a positive group (RPMI-1640 culture medium containing 0.64% phenol), B is control sample of a negative group (RPMI-1640 complete culture medium), C and D are test samples (extractants of chitosan complex films CS/SP1 and CS/SP5 with PPMI-1640 culture medium).

FIG. 8 shows micrographs of 3T3 cells after incubation under the conditions described above. A: positive group (RPMI-1640 culture medium containing 0.64% phenol), B: positive group (RPMI-1640 complete culture medium), C and D: test group (diluted extractants of chitosan complex films CS/SP1 and CS/SP5 in RPMI-1640 culture medium)

It can be observed in part (A) of FIG. 8 that almost all the control samples of 3T3 cells in the positive group are dead whereas cells in the negative group and samples in test group are still in a good condition exhibiting good cellular adherence and normal morphology of fully three-dimensional nuclei. The calculated cell viability is over 80% for the negative group and the test group, therefore, the chitosan complex films prepared by the method of the present disclosure have no or minimal influence on the growth of cells and are seemly safe for in vivo medical uses.

In summary, the present disclosure provides a method of preparing a chitosan complex film. The method first obtains modified PVA-124 by a reaction between PVA-124 and butanedioic anhydride, transforming hydroxyl radicals to carboxyl radicals. Different extents of carboxylation of SP (SP1, SP2, SP3, SP4, or SP5 of modified PVA-124) are mixed with chitosan (CS) into a homogeneous solution where CS and SP interact with each other via polyelectrolyte reactions. Finally, the chitosan complex film is formed by casting the homogeneous solution. The complex chiton film has better mechanical properties such as high tensile strength, larger elongation at break, stronger hydrophilicity and lower cytotoxicity than category 1 when compared with the pure chitosan film. Such characteristics enables potential applications in medical uses for anti-adhesion.

In the above disclosure, reference has been made to the accompanying drawings, which form a part hereof, and in which is shown by way of illustration specific implementations in which the present disclosure may be practiced. It is understood that other implementations may be utilized and structural changes may be made without departing from the scope of the present disclosure.

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described exemplary embodiments, but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching. Further, it should be noted that any or all of the aforementioned alternate implementations may be used in any combination desired to form additional hybrid implementations of the present disclosure.

The invention claimed is:

1. A method of preparing a chitosan complex film, the method comprising steps of:
    (1) obtaining a modified polyvinyl alcohol-124 (PVA-124) by reacting a PVA-124 with a butanedioic anhydride;
    (2) formulating an aqueous solution containing the modified PVA-124 and adding dropwise the aqueous solution of the modified PVA-124 into an acetic solution containing a chitosan to obtain a mixed solution;
    (3) adjusting a pH value of the mixed solution to a predetermined value with a NaOH solution;
    (4) obtaining a casting solution by removing surface bubbles of the mixed solution; and
    (5) pouring the casting solution into a culture dish and drying the culture dish with the casting solution to obtain a chitosan complex film.

2. The method of claim 1, wherein the step (1) comprises:
    formulating a first solution containing 20 wt % of the PVA-124 in a dimethylsulfoxide solvent and a second solution containing 20 wt % of the butanedioic anhydride in another dimethylsulfoxide solvent respectively;
    titrating the second solution containing 20 wt % of the butanedioic anhydride into the first solution containing 20 wt % of the PVA-124 to form a titrated mixture, wherein the titrated mixture is formulated according to a ratio of a first —OH mole number of the butanedioic anhydride to a second —OH mole number of the PVA-124;
    stirring the titrated mixture at 75° C. and 800 rounds/min for 5 hours;
    cooling the titrated mixture to a room temperature and adding dropwise the titrated mixture into a corresponding ethanol solution containing 5~10 wt % of NaOH to form precipitates of the modified PVA-124; and
    rinsing the precipitates of the modified PVA-124 repeatedly and drying the precipitates of the modified PVA-124 in a vacuum at 50° C. until no change in weight.

3. The method of claim 1, wherein the step (2) comprises:
    obtaining the mixed solution by titrating the aqueous solution containing the modified PVA-124 into the acetic solution containing the chitosan, wherein the mixed solution comprises an equal mass of the aqueous solution and the acetic solution.

4. The method of claim 1, wherein the step (2) further comprises:
    dissolving 0.4 wt % of the modified PVA-124 into deionized water in formulating the aqueous solution containing the modified PVA-124;
    dissolving 0.4 wt % of the chitosan in 1 wt % acetic acid in formulating the acetic solution containing the chitosan;
    filtering the acetic solution containing 0.4 wt % of the chitosan with a filter to remove a fractional amount of insoluble impurities;
    titrating the aqueous solution containing 0.4 wt% of the modified PVA-124 into the acetic solution containing 0.4 wt% of the chitosan; and
    stirring the mixed solution at 1000 rounds/minute to form a homogeneous mixture.

5. The method of claim 1, wherein the step (3) further comprises:
    adjusting a pH value of the mixed solution to pH 5.5 with a 0.1 wt % NaOH solution.

6. The method of claim 1, wherein the step (4) further comprises:
    obtaining a casting solution by removing surface bubbles of the mixed solution after one hour standing of the mixed solution.

7. The method of claim 1, wherein the step (4) further comprises:
    drying the cultured dish with the casting solution at 60° C. until no change in weight.

* * * * *